(12) United States Patent
Würtzen et al.

(10) Patent No.: US 7,867,715 B2
(45) Date of Patent: Jan. 11, 2011

(54) METHOD OF EVALUATING THE IMMUNOLOGICAL ACTIVITY OF A VACCINE

(75) Inventors: Peter A Würtzen, Vedbæk (DK); Gitte Lund, Allerød (DK); Henrik H. Jacobi, Vedbæk (DK); Hans-Henrik Ipsen, Hillerød (DK)

(73) Assignee: ALK-Abello A/S, Horsholm (DK)

( * ) Notice: Subject to any disclaimer, the term of this patent is extended or adjusted under 35 U.S.C. 154(b) by 0 days.

(21) Appl. No.: 10/901,938

(22) Filed: Jul. 28, 2004

(65) Prior Publication Data
US 2005/0069868 A1    Mar. 31, 2005

Related U.S. Application Data

(60) Provisional application No. 60/493,020, filed on Aug. 5, 2003.

(51) Int. Cl.
*G01N 33/53* (2006.01)
*A61K 49/00* (2006.01)
*A61K 39/395* (2006.01)

(52) U.S. Cl. ............ 435/7.1; 424/9.2; 424/130.1; 424/134.1; 424/171.1; 424/184.1; 424/193.1; 435/4; 435/174; 436/501; 436/518

(58) Field of Classification Search ........... 424/9.1, 424/9.2, 130.1, 134.1, 171.1, 184.1, 193.1; 435/4, 7.1, 174; 436/501, 518
See application file for complete search history.

(56) References Cited

U.S. PATENT DOCUMENTS 4,127,385 A    11/1978    Weeke

FOREIGN PATENT DOCUMENTS

| WO | WO-9411734 A1 | 5/1994 |
|---|---|---|
| WO | WO-9948525 A1 | 9/1999 |
| WO | WO-0151926 A2 | 7/2001 |
| WO | WO-2004038417 A1 | 5/2004 |

OTHER PUBLICATIONS

Katz, Jonathan B., et al., "In vitro assessment of viral antigen content in inactiviated aluminum hydroxide adjuvanted vaccines", Journal of Virological Methods, 1989, vol. 25, No. 1, pp. 101-108.
Thraenhart, Olaf, et al., "Standardization of an enzyme immunoassay for the in vitro potency assay of inactivated tissue culture rabies vaccines: determination of the rabies virus glycoprotein with polyclonal antisera", Journal of Biological Standardization (1989), vol. 17, No. 4, pp. 291-309.
Database WPI, Derwent Publications Ltd., XP002170319, AN 1993-212602, Jul. 7, 1992, Abstract.
Katz, J., "Desorption of Porcine Parvovirus from Aluminum Hydroxide Adjuvant with Subsequent Viral Immunoassay or Hemagglutination Assay", Veterinary Research Communications, vol. 11, No. 1, 1987, pp. 83-92.
Lacey, C.J.N., et al., "Phase IIa Safety and Immunogenicity of a Therapeutic Vaccine, TA-GW, in Persons with Genital Warts", Journal of Infectious Diseases, vol. 179, No. 3, Mar. 1999, pp. 612-618.
Krishnan, Lakshmi, et al., "Archaeosome Vaccine Adjuvants Induce Strong Humoral, Cell-Mediated, and Memory Responses: Comparison to Conventional Liposomes and Alum", Infection and Immunity, vol. 68, No. 1, Jan. 2000, pp. 54-63.
Desbordes, J., "Problems Raised by Potency Evaluation of Allergen Preparations", Developments in Biological Standardization, vol. 29, 1975, pp. 219-226.
Hoffmann, A., et al., "Determination of the allergenic activity of birch pollen and apple prick test solutions by measurement of B-hexosaminidase release from RBL-2H3 cells. Comparison with classical methods in allergen standardization", Allergy, vol. 54, No. 5, May 1999, pp. 446-454.
HogenEsch, Harm, et al., "Mechanisms of stimulation of the immune response by aluminum adjuvants", Vaccine, vol. 20, May 31, 2002, pp. S34-S39.
Demoly, P., et al., "Allergen-induced mediator release tests", Allergy, vol. 58, No. 7, Jul. 2003, pp. 553-558.
Levings, R.L., et a., "In vitro potency assays for nonreplicating veterinary vaccines: comparison to in vivo assays and considerations in assay development", Veterinary Microbiology, vol. 37, No. 3-4, 1993, pp. 201-219.
Marsh et al., "Studies on 'Allergoids' Prepared from Naturally Occurring Allergens," Immunology, 18, 705 (1970).
Wurtzen et al., "Chemical Modification of Birch Allergen Extract Leads to a Reduction in Allergenicity as well as Immunogenicity," Int Arch Allergy Immunol, 144:287-295 (2007).

(Continued)

*Primary Examiner*—Rodney P. Swartz
(74) *Attorney, Agent, or Firm*—Fish & Richardson P.C.

(57) ABSTRACT

The invention relates to an in vitro method of evaluating the immunological activity of a vaccine preparation in the form of a mixture of a molecular antigen and a carrier, wherein the mixture comprises a liquid phase and a solid phase, to which at least a part of the antigen is attached, the method comprising the steps of
i) subjecting the vaccine to one or more measurements; and
ii) using the measurement results to evaluate the immunological activity of the vaccine.

26 Claims, 4 Drawing Sheets

OTHER PUBLICATIONS

Gehlhar et al., "Characterization of Modified Allergen Extracts by in vitro B-Hexosaminidase Release from Rat Basophils," Int Arch Allergy Immunol, 136:311-319 (2005).

Corbel et al., "Workshop on Standardisation of Aluminum Adsorbed Vaccines", Biologicals (1997) 25, 351-353.

Yamamoto et al., "Quantitation of Group-specific α Antigen in Hepatitis B Vaccines by Anti-HBs/a Monoclonal Antibody", Biologicals (1997) 25, 973-980.

Shi et al., "Detoxification of endotoxin by aluminum hydroxide adjuvant", Vaccine 19 (2001) 1747-1752.

Maa et al., "Optimization of an Alum-Adsorbed Vaccine Powder Formulation for Epidermal Powder Immunization", Pharmaceutical Research, vol. 20 (2003), No. 7: 969-977.

Shi et al., "Change in the degree of adsorption of proteins by aluminum-containing adjuvants following exposure to interstitial fluid: freshly prepared and aged model vaccines", Vaccine 20 (2002) 80-85.

Geissler et al., "Quality Control and Stability of Chemically and Physically Modified Allergen Extracts", Arbeiten aus der Paul-Ehrlich-Institut, 87:191-7 (1994).

Poulsen et al., "Aluminum Hydroxide Adsorbed Allergens Used in Modified RAST", Allergy (1985), 40, 405-416.

Notice of Opposition to a European Patent; Patent No. 1649287; Opponent Novartis Vaccines & Diagnostics, Inc. (May 11, 2009)—14 pages.

Notice to opposition to a European Patent; Patent No. 1649287; Opponent Stallergenes S.A. (May 8, 2009)—42 pages (includes English translation).

Definition of alum adjuvant—National Cancer Institute Drug Dictionary.

Auszyme® FDA approval label (published Dec. 2001).

Reply of the Patent proprietor to the notice(s) of opposition to EP 1 649 287.

FIG. 1 Inhibition of the binding of IgE to biotinylated Phl p by Phl p or Alutard formulations.

METHOD OF EVALUATING THE IMMUNOLOGICAL ACTIVITY OF A VACCINE

CROSS-REFERENCE TO RELATED APPLICATIONS

This application claims the benefit of U.S. Provisional Application No. 60/493,020, filed Aug. 5, 2003.

TECHNICAL FIELD

The present invention relates to an in vitro method of evaluating the immunological activity, including the allergenic activity and potential for inducing allergic reactions, i.e., potential for inducing anaphylaxis, of a vaccine preparation in the form of a mixture of an antigen and a solid phase carrier, wherein the mixture comprises a liquid phase and a solid phase, to which at least a part of the antigen is attached.

BACKGROUND OF THE INVENTION

Vaccines for, e.g., subcutaneous injection may be prepared by mixing an aqueous solution of an antigen and a solid phase carrier, e.g. aluminum hydroxide gel, to produce a mixture, wherein at least a part of the antigen is adsorbed to the solid phase and part of or none of the antigen is in the liquid phase. The solid phase carrier may serve as an adjuvant, i.e. it potentiates the immune response of the antigen, although the mechanism of the potentiation is not always fully understood. Also, the mechanism and nature of the adsorption of the antigen to the solid phase carrier is not always fully understood and may depend strongly on the type of antigen involved. Theoretically, however, the adsorption to aluminum hydroxide gels partly involves electrostatic forces. For proteins, it is believed that the phosphate groups of phosphorylated proteins also interact with the aluminum hydroxide gel and possibly to some extent replaces the hydroxide groups in the gel structure.

Consequently, the degree of adsorption varies with the nature of the specific protein in question. Also, in the case of an antigen in the form of an extract of a biological material, e.g. an extract of grass pollen allergens, the extract contains a number of different ions and molecules, which potentially interferes with the bonding of the allergens to the solid phase carrier.

The immunological activity may be measured in an in vivo method involving the administration of the vaccine to a test animal to raise antibodies to the antigen, collecting a biological sample and assaying the sample to measure the amount of antibodies raised. The allergenic activity and the potential for inducing allergic reactions may be tested by intradermal injection in sensitized animals, and by measurement of the extent of the wheel and flare reactions (Kildsgaard et al., Assessment of the in vivo allergenic potency of new allergy vaccines by intradermal testing in sensitized mice, Clinical Immunology and Allergy in Medicine, Proceedings of the 21$^{st}$ EAACI Congress 2002, Naples, Italy). However, such in vivo methods are laborious and time-consuming, and they necessitate the use of test animals, which is undesirable.

Russian Patent No. SU-A-1 746 318 discloses a method of quantitative determination of antigen in tick-borne encephalitis vaccine preparation, wherein the antigen is adsorbed on aluminum hydroxide, the method comprising reacting the vaccine preparation with an excess amount of specific antibodies in phosphate buffer, followed by immunoenzymatic determination of the amount of antibodies in the supernatant. A calibration graph is used to obtain quantitative results.

Chang et al. (Vaccine 19 (2001) 2884-2889) discloses a study examining the degree of lysozyme adsorption to aluminum hydroxide gel in the vaccine and in interstitial fluid and its effect on the immune response in rabbits. Vaccines were pre-treated with phosphate anion to produce vaccines having degrees of adsorption ranging from 3 to 90%. It was found that the degree of adsorption of vaccines exhibiting 3, 35 or 85% adsorption changed to 40% within one hour of mixing with interstitial fluid to simulate subcutaneous administration. In accordance with this, the anti-lysozyme antibody response was the same for vaccines having different degrees of adsorption.

Shi et al. (Vaccine 20 (2002) 80-85) discloses a study of the ability of interstitial fluid to change the degree of adsorption of ovalbumin to aluminum hydroxide adjuvant and lysozyme to aluminum phosphate adjuvant. Ovalbumin and lysozyme were almost completely eluted after exposure at 37° C. to lymph fluid. The ability of lymph fluid to elute lysozyme from aluminum phosphate adjuvant did not change as the vaccine aged. Only 60% of the ovalbumin adsorbed to aluminum hydroxide was eluted during exposure to lymph fluid after the vaccine aged for 11 weeks at 4° C.

Iyer et al. (Vaccine 21 (2003) 1219-1223) discloses the finding that ovalbumin and dephoshorylated alpha casein were adsorbed in an aluminum hydroxide vaccine but were completely eluted when exposed to interstitial fluid. The vaccine nevertheless produced immunopotentiation compared to a solution of the protein. In contrast, alpha casein was completely adsorbed to aluminum hydroxide in both the vaccine and upon exposure to interstitial fluid. Immunopotentiation by aluminum hydroxide was also observed for alpha casein. The results indicated that antigen presenting cells can take up desorbed antigen from interstitial fluid as well as antigen adsorbed to aluminum-containing adjuvants.

Katz et al. (Journal of Virological Methods, 25 (1989) 101-108) discloses an ELISA for assessing the antigenic content of inactivated aluminum hydroxide adjuvanted virus vaccines. The ELISA is stated to supplement in vivo testing. Other in vitro methods comprise radioimmunoassay and methods requiring antigen desorption from aluminum hydroxide. Unlike such in vitro methods the ELISA did not suffer significant interference from the aluminum hydroxide except at high aluminium aluminum hydroxide concentrations. It is mentioned that previous attempts at an ELISA of intact vaccines suffered extreme inhibition by aluminum hydroxide. The article sets forth various explanations why the present ELISA works. In the ultimate paragraph it is suggested that the method may be applicable to aluminum hydroxide adjuvanted virus vaccines as a class.

Thraenhart et al. (Journal of Biological Standardisation, (1989) 17, 291-309) discloses an ELISA for in vitro potency testing of rabies virus vaccine by determination of rabies virus glycoprotein. The influence of aluminum hydroxide on the potency measurement was investigated and it was found that there was no influence.

U.S. Pat. No. 4,127,385 (Weeke) describes a method comprising mixing allergen extracts of horsehair and scale adhered to an alhydrogel with serum from an allergic patient to bind the free IgE of the serum to the allergen of the alhydrogel and subsequently adding radiolabelled anti-IgE and measuring the radioactivity. It is indicated that the method can be used to determine the strength or the storage life of allergen extracts adhered to alhydrogel. This type of prior art immunoassay has the disadvantage that antibodies not specific for the allergen will to a certain extent bind to the alhydrogel-allergen and result in an incorrect measurement.

The nature of molecular antigen adsorption to the solid phase carriers is very complex and largely unknown, and also it varies among different antigens depending on the chemical and structural nature of the antigen. Furthermore, the influence of the solid phase carrier in the reaction between antigen-specific IgE and antigen bound to a solid phase carrier is very complex and not fully known. Therefore, it has until now been believed that it is not possible to measure in vitro the immunological activity, including the allergenic activity and potential for inducing allergic reactions, of ready-to-use solid phase carrier vaccines comprising molecular antigens, or at least that it is not possible to measure it accurately. Thus, up to now it has been common practise practice to evaluate the immunological activity of a vaccine in vitro on the basis of a measurement of the immunological activity of the solution of molecular antigen used for the preparation of the ready-to-use solid phase carrier vaccine. The object of the present invention is to provide an in vitro method of evaluating the immunological activity of ready-to-use, solid phase carrier, molecular antigen vaccines.

SUMMARY OF THE INVENTION

This object is achieved with the present invention, which relates to the following aspects:

An in vitro method of evaluating the immunological activity of a vaccine preparation in the form of a mixture of a molecular antigen and a carrier, wherein the mixture comprises a liquid phase and a solid phase, to which at least a part of the antigen is attached, the method comprising the steps of
i) subjecting the vaccine to one or more measurements selected from the group consisting of:
1) the immunological activity of the mixture,
2) the immunological activity of antigen in the liquid phase,
3) the immunological activity of antigen in the solid phase,
4) the immunological activity of antigen in the liquid phase upon a treatment of the mixture to displace the antigen from the solid phase, and
5) the immunological activity of antigen in the solid phase upon a treatment of the mixture to displace the antigen from the solid phase,
wherein the immunological activity measurement is selected from the group consisting of a) antibody binding capacity using an immunoassay employing an antigen-specific antibody bound to an antibody solid phase, b) ability to activate effector cells and c) potential for inducing anaphylaxis; and
ii) using the measurement results to evaluate the immunological activity of the vaccine.

A method of preparing a vaccine preparation in the form of a mixture of an antigen and a solid phase carrier, wherein the mixture comprises a liquid phase and a solid phase, to which at least a part of the antigen is attached, the method comprising
i) mixing the antigen and the carrier,
ii) measuring the immunological activity of the vaccine using the method of evaluating the immunological activity of a vaccine preparation according to the invention, and
iii) repeating steps i) and ii) until a desired immunological activity is obtained.

A vaccine obtainable by the method of preparing a vaccine preparation according to the invention.

The present invention is based on the novel and surprising finding that it is indeed possible to perform measurements of the immunological activity, including the allergenic activity and potential for inducing allergic reactions, i.e., potential for inducing anaphylaxis, on ready-to-use solid phase carrier, e.g. gel, vaccines, using e.g. conventional competitive immunoassays, histamine release assays and T cell proliferation assays, without the solid phase carrier prevents valid and meaningful measurements to be made. In particular, the present invention is based on the novel and surprising finding that when the immunological activity is measured as the antibody binding capacity, it is possible to avoid the disturbing influence on the measurement by the solid phase carrier by using antibody bound to an antibody solid phase. It is believed that the reason for this is that the antibody solid phase prevents unspecific binding of antibody to the antigen-solid phase carrier system. This finding is surprising, since it might well be expected that it would be difficult for antibodies coupled to an antibody solid phase to obtain contact with the antigens of an antigen-solid phase carrier system. The same considerations apply to the situation, where the immunological activity is measured as the ability to activate effector cells, wherein the antigen-specific antibodies are bound to the effector cells, e.g. mast cells and basophils, which resemble a particulate antibody solid phase.

The invention is further based on the recognition that the problem of the complexity and uncertainties of the nature of antigen adsorption to solid phase carriers and the variability from one type of antigen to another can be eliminated 1) by comparing the measurement results obtained with historical results from the same type of antigen, 2) by relating measurement results for stored vaccines with results for the freshly prepared vaccine, and/or 3) by obtaining a detailed characterization of the vaccine by measuring a number of characteristic parameters of the vaccine, including the distribution of antigen between the liquid phase and the solid phase and the strength of the adsorption of the antigen to the solid phase carrier.

DETAILED DESCRIPTION OF THE INVENTION

Antigen

Figure 1:
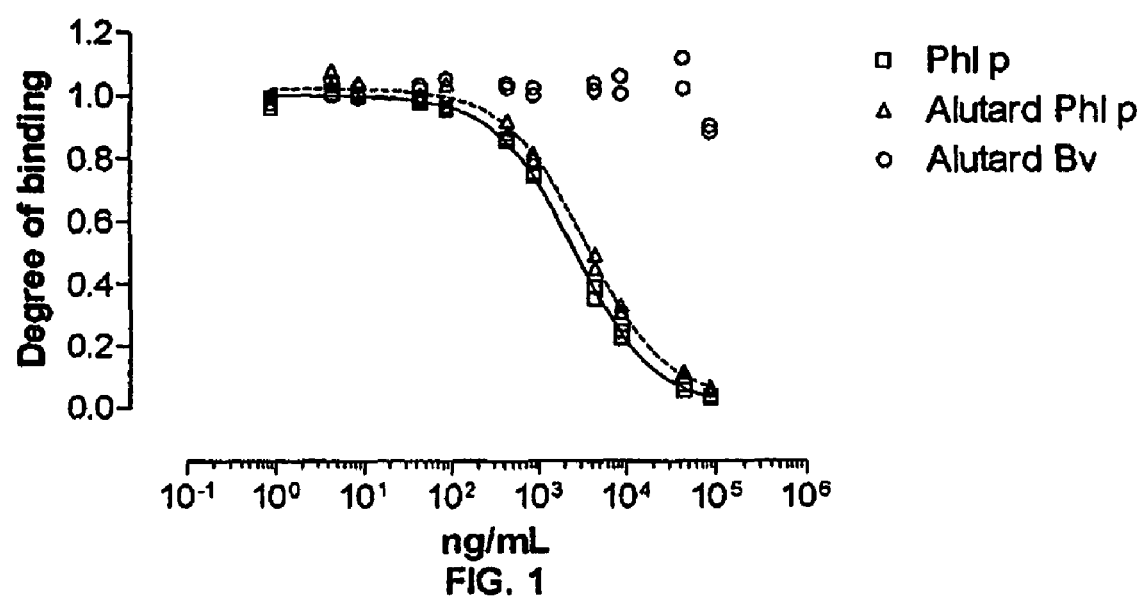
FIG. 1 shows the ability of Phl p extract adsorbed to an aluminum hydroxide gel (Alutard Phl p) to inhibit the binding of IgE to biotinylated Phl p extract using Phl p extract in solution (Phl p) as reference and Bet v extract (Alutard Bv) as negative control.

In connection with the present invention "antigen" means any immunogenic substance, i.e. any substance capable of activating the immune system.

In connection with the present invention "molecular antigen" means any substance in the form of a single molecule or a mixture of single molecules, wherein the single molecules may e.g. be proteins, carbohydrates, nucleotides and lipids as well as analogues and derivatives thereof. The expression "molecular antigen" excludes viral and microbial cells, such as bacterial and fungal cells.

The antigen may i.e., be selected from the group consisting of allergens, medicaments, nutritional substances and nucleotides, as well as analogues or derivatives thereof.

Examples of antigens are allergens, allergoids, peptides, haptens, carbohydrates and peptide nucleic acids (PNAs, a sort of synthetic genetic mimic), as well as analogues or derivatives thereof. Examples of nutritional substances are vitamins, enzymes, trace elements, and trace minerals as well as analogues or derivatives thereof. Examples of medicaments are antibodies, antibiotics, peptides, salts, hormones, hemolytics, hemostatics, enzymes, enzyme inhibitors, psycopharmica, opiates, and barbiturates, as well as analogues or derivatives thereof.

In the present context, the term analogues or derivatives is intended to include modified forms of the biologically active substance. The modification can be made by chemical modification or synthetic modification, e.g. by biotinylation, deamination, maleination, substitution of one or more amino acids, by cross-linking, by glycosylation, or by other recombinant technology. The term is also intended to include natural-occurring mutations, isoforms and retroinverse analogues.

The antigen may preferably be selected from the group consisting of:

nutritional substances like vitamins such as vitamin B12, vitamin B6, vitamin A, vitamin E, vitamin D, vitamin D3, iron, and folic acid;

enzymes such as urokinase, TPA (tissue plasminogen activator), coagulation Factor VIII, and streptokinase;

immunogenic substances such as natural, recombinant or modified proteins or fragments thereof, antigens, allergens (cf. below), allergoids, peptides, haptens conjugated on a suitable carrier like KLH (hey hole limpet hemocyanin) or Tetanus toxoid, carbohydrates, optionally inactivated or attenuated bacteria or virus as well as components thereof, RNA, DNA, PNA, parasites or retroviruses, parasitic material, mycoplasma, or toxins, e.g. such derived from Tetanus toxoid, Diphtheria toxoid, Cholera toxin A and B subunits, Rubella, Rhabdovirus (rabies), Myoxoviruses, Paramyoxyviruses like parainfluenza virus, mumps and meales, Picornaviruses like poliovirus, coxsackievirus, echovirus and rhinovirus, Reoviruses, Poxviruses like small pox virus, Vaccinia virus and cowpox virus, Papovaviruses like polyoma virus, papilloma virus and SV-40, Adenoviruses, EBV like mononucleosis virus, Parvoviruses like HPV B19, Herpes viruses like Herpes simplex virus, and Herpes zoster virus (Varicella virus), Cytomegalovirus (CMV), Arboviruses like yellow fever and Dengue fever, Retroviruses like HIV, Hepatitis viruses like Hepatitis A, Hepatitis B and Hepatitis C, *Haemophilus influenzae* type B, *Mycobacterium* like *M. tuberculosis, M. bovis, M. africanum, M. microti, M. avium, M. intracellulare, M. kansasii, M. gordonae, M. paratuberculosis*, and *M. lepramurium, Borrelia* spp. like *B. burgdorferi*, in particular *B. burgdorferi* sensu lato and *B. burgdorferi* sensu stricto, *B. garinii, B. afzelii, B. duttoni* and *B. recurrentis, Bordetella pertussis* (whooping cough), *Salmonella* spp. like *S. typhimurium* and *S. typhi, Treponema* spp. like *T. pallidum, Leptospira* spp., *Campylobacter* spp. like *C. jejuni, Helicobacter* spp. like *H. pylori, Pseudomonas* spp.,

*Legionella* spp., *Neisseria* spp. like *N. gonorrhoea* and *N. menigitidis, Chlamydia* spp. like *C. trachomatis, C. pneumonia* and *C. psittae, Enterobacter* spp., *Klebsiella* spp., *Yersinia* spp., *Vibrio* spp. like *Vibrio cholerae, Gardnerella* spp., *Rickettsia* spp., *Clostridium* spp. like *C. difficile, C. botulinum* and *C. tetani, Lactobacillus* spp., *Listeria* spp., and *Mycoplasma* spp. like *M. pneumoniae M. hominis, Plasmodium falciparum*, and *Leishmania donovani*, moulds and fungi such as *Clahdosporium, Alternaria, Aspergillus, Besidiomycetes, Candida albicans*, and *Penicillinum*, allergoids such as glutaraldehyde modified allergen complexes;

medicaments such as β-lactams e.g. penicillin, sulpha-containing preparations, enzymes, enzyme inhibitors e.g. acetylcholin esterase inhibitor, hormones e.g. LHRH, estrogen, insulin and human growth hormone, hemolytics/hemostatics e.g. heparin, and erythropoetrin α or β, psycopharmica e.g. lithium, opiates e.g. morphine, and barbiturates;

genetic material such as DNA, RNA, and PNA;

other medicaments like cancer-related compounds, such as TNFα, LHRH analogues, cytostatica, and anti-cancer antibodies, such as antibodies against breast cancer cells, e.g. antibodies against HER-2 receptor, colon cancer cells, and B cell lymphoma cells, e.g. antibodies against CD20 on malign B cells;

other compounds such as sugars, mannans and lectins;

as well as analogues or derivatives thereof.

In a preferred embodiment of the invention the antigen is an allergen. In a preferred embodiment of the invention the allergen is any naturally occurring protein that has been reported to induce allergic, i.e. IgE mediated reactions upon their repeated exposure to an individual. Examples of naturally occurring allergens include pollen allergens (tree-, herb, weed-, and grass pollen allergens), insect allergens (inhalant, saliva and venom allergens, e.g. mite allergens, cockroach and midges allergens, hymenoptera venom allergens), animal hair and dandruff allergens (from e.g. dog, cat, horse, rat, mouse etc.), and food allergens. Important pollen allergens from trees, grasses and herbs are such originating from the taxonomic orders of Fagales, Oleales, Pinales and platanaceae including i.a. birch (Betula), alder (Alnus), hazel (Corylus), hornbeam (Carpinus) and olive (Olea), cedar (Cryptomeria and Juniperus), Plane tree (Platanus), the order of Poales including i.a. grasses of the genera Lolium, Phleum, Poa, Cynodon, Dactylis, Holcus, Phalaris, Secale, and Sorghum, the orders of Asterales and Urticales including i.a. herbs of the genera Ambrosia, Artemisia, and Parietaria. Other important inhalation allergens are those from house dust mites of the genus *Dermatophagoides* and *Euroglyphus*, storage mite e.g *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (superfamily Apidae), wasps (superfamily Vespidea), and ants (superfamily Formicoidae). Important inhalation allergens from fungi are i.a. such originating from the genera *Alternaria* and *Cladosporium*.

In a more preferred embodiment of the invention the allergen is Bet v1, Aln g 1, Cor a 1 and Car b 1, Que a 1, Cry j 1, Cry j 2, Cup a 1, Cup s 1, Jun a 1, Jun a 2, jun a 3, Ole e 1, Lig v1, Pla l 1, Pla a 2, Amb a 1, Amb a 2, Amb t 5, Art v 1, Art v 2 Par j 1, Par j 2, Par j 3, Sal k 1, Ave e 1, Cyn d 1, Cyn d 7, Dac g 1, Fes p 1, Hol l 1, Lol p 1 and 5, Pha a 1, Pas n 1, Phl p 1, Phl p 5, Phl p 6, Poa p 1, Poa p 5, Sec c 1, Sec c 5, Sor h 1, Der f 1, Der f 2, Der p 1, Der p 2, Der p 7, Der m 1, Eur m 2, Gly d 1, Lep d 2, Blo t 1, Tyr p 2, Bla g 1, Bla g 2, Per a 1, Fel d 1, Can f 1, Can f 2, Bos d 2, Equ c 1, Equ c 2, Equ c 3, Mus m 1, Rat n 1, Apis m 1, Api m 2, Ves v 1, Ves v 2, Ves v 5, Dol m 1, Dil m 2, Dol m 5, Pol a 1, Pol a 2, Pol a 5, Sol i 1, Sol i 2, Sol i 3 and Sol i 4, Alt a 1, Cla h 1, Asp f 1, Bos d 4, Mal d 1, Gly m 1, Gly m 2, Gly m 3, Ara h 1, Ara h 2, Ara h 3, Ara h 4, Ara h 5 or shufflant hybrids from molecular breeding of any of these.

In the most preferred embodiment of the invention the allergen is grass pollen allergen or a dust mite allergen or a ragweed allergen or a cedar pollen or a cat allergen or birch allergen.

In yet another embodiment of the invention the vaccine comprises at least two different species of allergens either originating from the same allergic source or originating from different allergenic sources e.g. grass group 1 and grass group 5 allergens or mite group 1 and group 2 allergens from different mite and grass species respectively, weed antigens like short and giant ragweed allergens, different fungis allergens like alternaria and cladosporium, tree allergens like birch, hazel, hornbeam, oak and alder allergens, food allergens like peanut, soybean and milk allergens.

The allergen incorporated into the vaccine may be in the form of an extract, a purified allergen, a modified allergen, a recombinant allergen or a mutant of a recombinant allergen. An allergenic extract may naturally contain one or more isoforms of the same allergen, whereas a recombinant allergen typically only represents one isoform of an allergen. In a preferred embodiment the allergen is in the form of an extract. Preferably, the immunological activity of two or more major and/or minor allergens of the extract is measured. In addition the immunological activity of the whole extract may be measured.

In another preferred embodiment the allergen is a recombinant allergen. In a further preferred embodiment the allergen is a naturally occurring low IgE-binding mutant or a recombinant low IgE-binding mutant.

Allergens may be present in equi-molar amounts or the ratio of the allergens present may be in the range of from 1:1 to 1:40, preferably from 1:1 to 1:20 and more preferably from 1:1 to 1:10.

In a further embodiment of the invention the low IgE binding allergen is an allergen according to WO 99/47680 or WO 02/40676.

Solid Phase Carrier

The solid phase carrier may be any water-insoluble substance capable of forming a covalent and/or a non-covalent attachment with an antigen, wherein the non-covalent attachment includes e.g. adherence, inclusion, encapsulation and coupling.

The carrier may be a gel forming agent, including an oxygen-containing metal salt and an encapsulating agent, liposomes, oil-in-water emulsions and ISCOMs, preferably oxygen-containing metal salts.

Preferably, the carrier is an adjuvant.

Examples of suitable oxygen-containing metal salts are e.g. those, wherein the cation is selected from Al, K, Ca, Mg, Zn, Ba, Na, Li, B, Be, Fe, Si, Co, Cu, Ni, Ag, Au, and Cr.

The anion of the oxygen-containing compound may be an organic or inorganic anion, or a combination of organic and inorganic anions. Examples of suitable oxygen-containing metal salts are e.g. those, wherein the anion selected from sulphates, hydroxides, phosphates nitrates, iodates, bromates, carbonates, hydrates, acetates, citrates, oxalates, and tartrates, as well as mixed forms thereof. The oxygen-containing metal salts further comprise coordination complexes. A definition of coordination complexes is given in e.g. The Handbook of Chemistry and Physics 56 Ed., Section B, Chapter 7 (1975-76).

Within the present context, the expression “mixed forms” is intended to include combinations of the various anions as well as combinations with e.g. chlorides, and sulphides.

Although the delivery system comprises an oxygen-containing metal salt, it is contemplated that the oxygen could be substituted by another Group VIA atom such as S, Se or Te.

The oxygen-containing metal salt to be used in accordance with the invention may be any oxygen-containing metal salt providing the desired effect when formulated into a mucosal delivery system. Examples of such oxygen-containing substances are aluminum hydroxide, aluminum phosphate, aluminum sulphate, potassium aluminum sulphate, calcium phosphate, Maalox (mixture of aluminum hydroxide and magnesium hydroxide), beryllium hydroxide, zinc hydroxide, zinc carbonate, zinc chloride and barium sulphate. Preferred oxygen-containing metal salts are aluminum hydroxide, aluminum phosphate and calcium phosphate.

Peyer’s patches are aggregates of lymphoid nodules located in the wall of the small intestine, large intestine and appendix and are an important part of body’s defense against the adherence and penetration of infection agents and other substances foreign to the body. Peyer’s patches are also known as folliculi lymphatic aggregati. Similar folliculi lymphatic aggregati can be found in the respiratory tract, the rectum, the nasal cavity, the oral cavity, the pharynx, the genitourinary tract, large intestine and other mucosal tissues of the body. The said tissues may in general be referred to as mucosally-associated lymphoid tissues (MALT).

It has been shown that pharmaceutically active substances formulated as microcapsules having a proper size and suitable physico-chemical properties may be effectively taken up by Peyer’s patches and MALT.

The use of microcapsules involves the advantage of protecting the pharmaceutical active substance from degradation, both during production and storage of the dosage forms, and in the process of administration of the active substance to the patient. This is particularly important, when the active substance is an allergen. The use of microencapsulation to protect sensitive bioactive substances from degradation has become well-known. Typically, a bioactive substance is encapsulated within any of a number of protective wall materials, usually polymeric in nature. The agent to be encapsulated can be coated with a single wall of polymeric material (microcapsules), or can be homogeneously dispersed within a polymeric matrix (microspheres). (Hereafter, the term microcapsules refers to both microcapsules and microspheres and the terms “encapsulation” and “microencapsulation” should be construed accordingly). The amount of substance inside the microcapsule can be varied as desired, ranging from either a small amount to as high as 95% or more of the microcapsule composition. The diameter of the microcapsule is preferably less than 20 μm, more preferably less than 15 μm, more preferably less than 10 μm and most preferably between 1 and 10 μm.

The encapsulating agent may be any biodegradable agent, preferably a polymeric agent. Preferably, the first encapsulating agent is selected from the group consisting of poly-lactide, poly-lactid-poly(ethylene glycol), poly(DL-lactide-co-glycolide), poly(glycolide), copolyoxalates, polycaprolactone, poly(lactide-co-caprolactone), poly(esteramides, polyorthoesters and poly(8-hydroxybutyric acid), and polyanhydrides, most preferably poly(DL-lactide-coglycolide). Other examples of encapsulating agents are poly (butyl-2-cyanoacrylate), poly(3-hydroxybutyrate) and polyanhydride copolymers of fumaric and sebacic acid, poly(FA:SA). Also, suitable encapsulating agents for use according to the present invention include those derived from animal or vegetable proteins, such as gelatines, dextrins and soy, wheat and psyllium seed proteins; gums such as acacia, guar, agar and xanthan; polysaccharides; starch and modified starch, alignates; carboxymethylcellulose; carrageenans; dextrans; pectins; synthetic polymers such as polyvinylpyrrolidone; and polypeptide/protein or polysaccharide complexes such as gelatine-acacia complexes. In one embodiment of the invention two or more encapsulating agents are used. Preferably, the encapsulating agent is selected so as to make the microparticles hydrophobic. It is believed that hydrophobic microparticles are more easily taken up by the MALT or allowed to elicit its effects via the MALT.

Examples of oil-in water emulsions are MF59, which is a squalene in water emulsion.

Liposomes are aqueous suspensions of spheroid vesicles, which are phospholipids organized in bilayer structures. Liposomes are generally composed of phospholipids and cholesterol. Any phospholipids may be used for the preparation of liposome vaccines. One example of a suitable phopholipid is dipalmitoyl phophatidylcholine. One example of a liposome vaccine composition is dipalmitoyl phophatidylcholine, cholesterol, diacetylphophate and antigen. Liposomes are classified according to size and properties as follows: Small unilamellar vesicles (SUV), Large unilamellar vesicles (LUV), LUV/reverse phase evaporation (REV), Large unilamellar vesicles by extrusion (LUVET), multilamellar vesicles (MLV), freeze and thaw multilamellar vesicles (FT-MLV), stable pluerilamellar vesicles (SPLV).

Saponins are the active component of a variety of lipid mixtures known as ISCOMs (Immunostimulating complexes). Saponins are sterol and triterpenoid glycosides derived from the bark of the Quilaja saponiaria tree. Examples of ISCOMs are Quil A and Qs-21.

Displacement of Antigen from the Solid Phase

In one embodiment of the invention, the displacing treatment comprises contacting the mixture with a protein-containing reagent. It is believed that the displacing potential increases with increasing electrochemical charge of the protein, and hence charged proteins are preferred. Any protein may be used to effect displacement of antigen from the solid phase carrier. Preferred protein-containing reagents are body fluids, such as lymph fluid, interstitial fluid, blood plasma, blood serum, purified fractions of body fluids and proteins isolated from body fluids, such as Human Serum Albumin (HAS). Preferably, the body fluid is blood serum. The use of body fluids for the displacement of antigen from the solid phase carrier makes it possible to simulate the in vivo conditions, which the vaccine is subjected to after administration.

In a second embodiment, the displacing treatment comprises contacting the mixture with anions, such as phosphate ions, citrate ions, lactate ions, acetate ions, sulphate ions, borate ions and oxalate ions, preferably, phosphate ions.

Preferably, the displacement is carried out at a pH of from 4 to 10, more preferably from 5 to 9, and most preferably from 6 to 8. Preferably, the displacement is carried out at a temperature of from 32° C. to 42° C., more preferably from 35° C. to 39° C., and most preferably from 36° C. to 38° C.

Measurement of Antibody Binding Capacity

In connection with the present invention the expression "antibody binding capacity" means the level of B cell epitopes available in the vaccine for antibody binding. The measurement of antibody binding capacity of the vaccine preparation may be carried out using any suitable method or immunoassay capable of performing such a measurement, wherein the antibody is bound to an antibody solid phase. Suitable types of assays include 1) assays wherein the antigen to be assayed is passively attached to a solid phase, and 2) assays wherein the antigen to be assayed is captured by a first antigen-specific antibody coupled to a solid phase. For both type 1) and 2) assays, the antigen attached to the solid phase may a) be reacted with a second antigen-specific antibody, or b) with a modified antigen.

When using option a), i) the second antigen-specific antibody may be labelled (direct assay) or ii) it may be reacted with a labelled anti-antibody specific to the second antigen-specific antibody (indirect assay). When using option b), the modified antigen may be labelled or be adapted to be coupled to a label, e.g. by a linker system. One example of such a linker system is the biotin-avidin/streptavidin system.

The label may be any suitable label system conventionally used in immunoassays comprising chromogenic labels, luminescent labels, chemiluminescent labels, enzyme labels, radioactivity labels, fluorescent labels, and absorbance labels, preferably chemiluminescent labels.

In a preferred embodiment of the invention, the label compound is a chemiluminescent compound covalently bound to avidin, streptavidin or a functional derivative thereof.

The chemiluminescent label is preferably an acridinium compound, such as dimethylacridiniumester (DMAE).

The first and second antigen-specific antibody and the anti-antibody may all independently of each other be either monoclonal or polyclonal.

The assay of type 2)a) is commonly referred to as a sandwich assay or a two-site assay. The assay of type b) is commonly referred to as an inhibition assay, when the antigen to be assayed is allowed to become attached to the solid phase prior to adding to modified antigen. The assay of type b) is commonly referred to as a competition assay, when the antigen to be assayed and the modified antigen are mixed prior to becoming attached to the solid phase.

In a preferred embodiment of the present invention, the immunoassay is a competitive assay or an inhibition assay, preferably a competitive assay.

In a preferred type of competitive immunoassay the immunological activity of a vaccine is measured as the degree of inhibition of the bonding between standardized biotinylated antigen and antigen-specific IgE by the antigen-containing vaccine. The immunoassay comprises the steps of 1) mixing the antigen-containing vaccine preparation with biotinylated antigen to form an antigen mixture, 2) incubating the antigen mixture with antigen-specific IgE coupled to an antibody solid phase, e.g. a particulate carrier, such as paramagnetic particles, to form an immunocomplex, and 3) optionally washing and subsequently incubating the immunocomplex with streptavidin labelled labeled with acridinium ester, and 4) washing and subsequently measuring the amount of light emitted. The immunoassay may be carried out using e.g. an ADVIA Centaur (Bayer).

Examples of suitable immunoassays are ELISA-based assays and RAST.

In a further suitable immunoassay for carrying out the method of the invention, 1) a quantified amount of antigen-specific antibody is reacted with the antigen vaccine to be assayed, 2) in the resulting reaction mixture, the liquid phase is separated from the solid phase, and 3) the remaining amount of unbound antibody in the liquid phase is measured. The measurement of antibody in the liquid phase may be carried out using any conventional method for quantifying antibody. In a variant of this immunoassay, the liquid phase is not separated from the solid phase before the measurement of unbound antibody.

The type of antibody used or detected in the immunoassay determines the type of epitopes measured. Thus, dependent on the type of antibody, e.g. IgA, IgE, IgG and IgM, used or detected it is possible to selectively measure IgA, IgE, IgG and IgM epitopes, respectively. In a preferred embodiment of the invention, the antibody used or detected is selected from the group consisting of IgA, IgE, IgG, IgM and combinations thereof. In a particular embodiment of the invention, the antibodies used or detected are both IgE and IgG. In a preferred embodiment of the invention, the antibody used or detected is IgE.

Antibody Solid Phase

The antibody solid phase may be any solid phase conventionally used in immunoassays, including microtiter plates and particles, e.g. paramagnetic particles.

Measurement of Ability to Activate Effector Cells

In a preferred embodiment of the method of the invention, the immunological activity is measured as the ability to activate effector cells of the immune system.

In one embodiment of the invention, whole blood is used for effector cell activation. In a second embodiment, the effector cells are cells isolated from a biological sample. In a third embodiment, the effector cells are cells isolated from a biological sample and cultivated. In a fourth embodiment, the effector cells are cells isolated from a biological sample, cultivated and modified, e.g. genetically modified.

Preferably, the effector cells are selected from the group consisting of mast cells, basophils, eosinophils, T cells, B cells and Antigen Presenting Cells (APC), and combinations thereof. Other preferred effector cells are modified effector cells, i.e. cells derived from and having at least some features of effector cells, including genetically modified cells and malignantly transformed cells.

In one embodiment of the invention, the effector cell activating ability is measured by measuring the level of an effector cell marker. The marker is preferably selected from the group consisting of secretory molecules, surface molecules and intracellular molecules. Preferably, the secretory molecule is selected from the group consisting of mediators, cytokines, cytotoxic proteins and soluble receptors.

Examples of the mediator to be measured are mediators selected from the group consisting of histamine, leucotrienes ($LTB_4$, $LTC_4$, $LTD_4$ and $LTE_4$), prostaglandines ($PGD_2$, $PGE_2$ and $PGF_{2\alpha}$), thromboxane, Platelet Activating Factor (PAF), Major Basic Protein (MBP), ECF, ECP, EDN, EPO, bradykinin, adenosine, Substance P, Neurokinin A, complement factors (e.g. C3d), including complement fragments; Serotonin, Oxygen Radicals, basogranulin, and mast cell and basophil proteases, including tryptase, chymase, carboxypeptidase and cathepsin.

Examples of the cytokine to be measured are cytokines selected from the group consisting of Interleukins (IL-1 to IL-27), hematopoietric growth factors, granulocyte-macrophage colony stimulating factors (e.g. CM-CSF), interferons (IFN$\alpha$, IFN$\beta$, IFN$\gamma$), tumor necrosis factor (TNF) related molecules (TNF and lymphotoxin), 1 g superfamily members (IL-1), the TGF-beta family and the chemokines (IL-8, RANTES and others). Assays for measuring the following cytokines are widespread: IL-2, IL-4, IL-5, IL-6, IL-10, IL-12, IL-13, IFN-gamma, TNF-alpha, TGF-beta.

Examples of the cytotoxic protein to be measured are cytotoxic proteins selected from the group consisting of Eosinophil Cationic Protein (ECP), Major Basic Protein (MBP) and EDN.

Preferably, the surface molecule is selected from the group consisting of surface receptors and adhesion molecules, such as selectins, integrins and the immunoglobulin superfamily (ICAM-1, VCAM-1), VLA4, CD11B, CD11C, CD18 and $\alpha$-d. Surface molecules known to be up- or downregulated in effector cells by antigen activation are CD23, CD69, CD203C (I-NPP3), CD31, CD162 and CD162L. Other surface molecules include basogranulin.

Preferably, the effector cell marker is histamine, tryptase, basogranulin, leucotrien $LTC_4$, CD63, CD69 and CD203C. Histamine may e.g. be measured in an ELISA-based method based on the competition between histamine to be assayed and its enzyme conjugate, histamine-alkaline phosphatase used as tracer for binding to antibody coated onto microwells. The monoamine histamine is too small to occupy completely the binding site on the antibody. High affinity monoclonal antibodies directed against modified histamine have therefore been obtained. The histamine in the sample must be derivatized in the same manner as the histamine of the conjugate. This is achieved readily and reproducibly with an acylating reagent at slightly alkaline pH. The acylated histamine of the sample, and the histamine-alkaline phosphatase conjugate, when added to the microtiter wells, compete for binding to a limiting number of antibody sites. After incubation, the wells are rinsed in order to remove non-bound components. The bound enzymatic activity is then measured by the addition of a chromogenic substrate (pNPP). The intensity of the color depends inversely on the concentration of histamine in the sample. The concentration is calculated on the basis of a standard curve obtained with standards. This enzyme immunoassay may be carried out using a kit obtainable from "IMMUNOTECH" (Marseille, France).

In a second embodiment of the invention, the effector cell activating ability is measured by measuring the T cell proliferation. The T cell proliferation may be measured by a method based on incorporation of 3H-thymidine or the reduction of fluorescence labelling and may be conducted using freshly isolated leucocytes from the blood of sensitized subjects or using established allergen-specific T-cell lines. In addition, the cytokine production of the activated cells may be investigated by analysis of the cell supernatants by ELISA or beads based methods.

Early events in the T-cell activation may be investigated through flow cytometric analysis of T-cell expression of different surface receptors such as CD25, 26, 27, 39, 45 RA/O, 69, 70, 96, 97, 108, 109, 134 (OX40), 153, 154 (OX40L), 166, 178 (FasL), 183 (CXCR3), 212 (IL-12Rb1), 223, which are up- or down-regulated at different time-points during T-cell activation.

The activation of T-cells may be influenced by the differentiation and activation stage of the antigen presenting cells (APC), which may be investigated by flow cytometric analysis of the following surface molecules: CD14, 25, 26, 40, 80/86, 83, 105, 166.

Finally, the immunological effect of the vaccines on B-cell activation may be described via the surface expression of CD25, 26, 39, 80/86, 97, 126, 138 and surface expression as well as secretion of different antibody isotypes. As an additional alternative the majority of the parameters described above may be investigated at the mRNA level through Taqman analysis, gene chip analysis, or other method for quantifying gene expression.

Measurement of Potential for Inducing Anaphylaxis

Administration of a vaccine involves a certain level of risk of eliciting IgE mediated side effects, e.g. anaphylaxis. In a particular aspect of the method of the invention, the immunological activity of the vaccine preparation is measured as the potential for inducing anaphylaxis. Preferably, the potential for inducing anaphylaxis is measured by measuring the level of an effector cell anaphylaxis marker selected from the group consisting of effector cell markers mentioned above. Preferably, the effector cell anaphylaxis marker is histamine, tryptase, basogranulin, leucotrien LTC4, CD63, CD69 and CD203C. Histamine is released from mast cells and basophils. Histamine may e.g. be measured in the ELISA-based method described above. Also, histamine may be measured using glass fibre based assays.

In a preferred embodiment of this aspect of the invention, the potential for inducing anaphylaxis in whole blood is measured. Preferably, the whole blood used for the measurement has been withdrawn from a subject maximally five hours, more preferably two hours, prior to the measurement.

It is preferred that the vaccine and the whole blood is mixed in a ratio corresponding to a calculated in vivo ratio, which would occur in a subject as a result of an accidental administration of a vaccine dose into the blood stream of a subject. Also, it is preferred that the whole blood adjusted to body temperature is used.

In an alternative embodiment of this invention, the potential for inducing anaphylaxis 1) in effector cells isolated from a biological sample, 2) in effector cells isolated from a biological sample and cultivated, or 3) in effector cells isolated from a biological sample, cultivated and modified, e.g. genetically modified, is measured.

Preferably, the effector cells are selected from the group consisting of mast cells, basophils, eosinophils, T cells, B cells and Antigen Presenting Cells (APC), and combinations thereof. Other preferred effector cells are modified effector cells, i.e. cells derived from and having at least some features of effector cells, including genetically modified cells and malignantly transformed cells. Geneticaly modified cells may e.g. be cells genetically modified so as to express one or more proteins, which are not expressed in native cells, including intracellular proteins and surface proteins, e.g. receptor proteins. Malignantly transformed cells may e.g. be a cancer cell line, e.g. a cancer cell capable of continuous in vitro growth without stimulation.

Immunological Activity Measurements 1)-5)

In one embodiment of the invention, the vaccine is subjected solely to a measurement of the immunological activity of the mixture of the liquid phase and the solid phase (measurement 1)).

In a second embodiment of the invention, the vaccine is subjected solely to a measurement of the immunological activity of antigen in the liquid phase upon a treatment of the mixture to displace the antigen from the solid phase (measurement 4)).

In a third embodiment of the invention, the vaccine is subjected both to a measurement of the immunological activity of the mixture of the liquid phase and the solid phase (measurement 1)), and to a measurement of the immunological activity of antigen in the liquid phase (measurement 2)).

In a fourth embodiment of the invention, the vaccine is subjected both to a measurement of the immunological activity of antigen in the liquid phase (measurement 2)), and to a measurement of the immunological activity of antigen in the solid phase (measurement 3)).

In a fifth embodiment of the invention, the vaccine is subjected both to a measurement of the immunological activity of the mixture of the liquid phase and the solid phase (measurement 1)), and to a measurement of the immunological activity of antigen in the liquid phase upon a treatment of the mixture to displace the antigen from the solid phase (measurement 4)).

Evaluation of Immunological Activity of Vaccine

A preferred embodiment of the method of the invention is one, wherein the immunological activity, including allergenic activity and potential for inducing allergic reactions, e.g. potential for inducing anaphylaxis, of an antigen-containing intermediate product used for preparing the vaccine is measured, and wherein the evaluation of the immunological activity of the vaccine is based on a comparison of the measurement result obtained for the intermediate product and the measurement results obtained for one or more of measurements 1)-5). Preferably, the vaccine is subjected to the measurements immediately upon preparation.

A further preferred embodiment of the invention is one, wherein the vaccine is subjected to the measurements immediately after preparation and after one or more periods of storage, and wherein the evaluation of the immunological activity of the vaccine is based on a comparison between the former and latter measurement results.

Yet a further embodiment of the invention is one, wherein the evaluation of the immunological activity of the vaccine is based on a comparison between the measurement results obtained for the vaccine and prior corresponding measurement results from the same type of vaccine or from another type of vaccine.

Vaccines

The vaccine preparation subjected to the method of the present invention may be any ready-to-use preparation in the form of a mixture of an antigen and a solid phase carrier, wherein the mixture comprises a liquid phase and a solid phase, to which a part of the antigen is attached, or any such preparation for preparing a ready-to-use formulation.

The ready-to-use preparation may be for parenteral administration and for mucosomal administration.

Parenteral administration includes intravenous, intramuscular, intraarticular, subcutaneous, intradermal, epicutaneous/transdermal and intraperitoneal administration. Vaccines for administration via injection may be formulated so as to be suitable for injection by needle or for needleless injection.

Mucosomal administration includes oral, nasal, vaginal, sublingual, ocular, rectal, urinal, intramammal, pulmonal, otolar (i.e. via the ear) or buccal administration.

The vaccine may be in the form of a spray, an aerosol, a mixture, a suspension, a dispersion, an emulsion, a gel, a paste, a syrup, a cream, an ointment, implants (ear, eye, skin, nose, rectal, and vaginal), intramammary preparations, vagitories, suppositories, or uteritories.

Method of Preparing a Vaccine

The present invention further relates to a method of preparing a vaccine preparation in the form of a mixture of an antigen and a solid phase carrier, wherein the mixture comprises a liquid phase and a solid phase, to which at least a part of the antigen is attached, the method comprising i) mixing the antigen and the carrier,
ii) measuring the immunological activity of the vaccine using any of methods below:
an in vitro method of evaluating the immunological activity of a vaccine preparation in the form of a mixture of a molecular antigen and a carrier, wherein the mixture has a liquid phase and a solid phase, to which at least a part of the antigen is attached, the method involving the steps of: i) subjecting the vaccine to one or more measurements selected from the group consisting of:
1) the immunological activity of the mixtures
2) the immunological activity of antigen in the liquid phase,
3) the immunological activity of antigen in the solid phase,
4) the immunological activity of antigen in the liquid phase upon a treatment of the mixture to displace the antigen from the solid phase, and
5) the immunological activity of antigen in the solid phase upon a treatment of the mixture to displace the antigen from the solid phase, wherein the immunological activity measurement is selected from the group consisting of a) antibody binding capacity using an immunoassay employing an antigen-specific antibody bound to an antibody solid phase, b) ability to activate effector cells and c) potential for inducing anaphylaxis; and
ii) using the measurement results to evaluate the immunological activity of the vaccine;

a method according to the method above, wherein the immunological activity is measured as the antibody binding capacity;

the antibody used or detected can be, for example, IgA, IgE, IgG, IgM and combinations thereof;

a method according to any of the above wherein the immunological activity is measured in an immunoassay, for example, a competitive immunoassay;

a method according to the above wherein the immunological activity is measured as the ability to activate effector cells of the immune system Whole blood can used for effector cells activation, and the effector cells can be cells isolated from a biological sample and cultivated, and/or modified. The effector cells can be mast cells, basophils, eosinophils, T cells, B cells and Antigen Presenting Cells (APC), and combinations thereof. The effector cell activating ability is measured by measuring the level of an effector cell marker, for example, secretory molecules, surface molecules and intracellular molecules. Secretory molecules are, for example, mediators, cytokines, cytotoxic proteins and soluble receptors. Mediators measured can be, for example, histamine, leucotrienes ($LTB_4$, $LTC_4$ $LTD_4$ and $LTE_A$), prostaglandines ($PGD_2$, $PGE_2$, and $PGF_{2a}$), thromboxane, Platelet Activating Factor (PAF), Major Basic Protein (MBP), ECF, ECP, EDN, EPO, bradykinin, adenosine, Substance P, Neurokinin A, complement factors (e.g. C3d), including complement fragments; Serotonin, Oxygen Radicals, basogranulin, and mast cell and basophil proteases, including tryptase, chymase, carboxypeptidase and cathepsin. Cytokines measured can be, for example, Interleukins (IL-1 to IL27), hematopoietric growth factors, granulocyte-macrophage colony stimulating factors (e.g. CM-CSF), interferons (IFNα, IFNβ, IFNγ), tumor necrosis factor (TNF) related molecules (TNF and lymphotoxin), Ig superfamily members (IL-1), the TGF-beta family and the chemokines (IL-8, RANTES and others). Cytotoxic proteins measured can be, for example, Eosinophil Cationic Protein (ECP), Major Basic Protein (MBP) and EDN. Surface molecules can be, for example, surface receptors and adhesion molecules, including selectins, integrins, the immunoglobulin superfamily (ICAM-1, VCAM-1), VLA4, CD11B, CD11C, CD18, α-d, CD23, CD69, CD203C (I-NPP3), CD31, CD162, CD162L and basogranulin;

the effector cell activating ability for these methods is measured by measuring the T cell proliferation;

a method of evaluating the immunological activity of a vaccine preparation, wherein the immunological activity is the potential for inducing anaphylaxis that is assessed by measuring the level of an effector cell anaphylaxis markers such as, for example, histamine, tryptase, basogranulin, leucotrien LTC4, CD63, CD69 and CD203C;

a method for measurement of the potential for inducing anaphylaxis in whole blood withdrawn from a subject maximally five hours prior to the measurement, or maximally two hours prior to the measurement;

a method according to the above wherein the vaccine and the whole blood is mixed in a ratio corresponding to a calculated in vivo ratio, which would occur in a subject as a result of an accidental administration of a vaccine dose into the blood stream of a subject;

a method wherein whole blood adjusted to body temperature is used;

a method for the measurement of the potential for inducing anaphylaxis in effector cells isolated from a biological sample. This method can be carried out in 1) in effector cells isolated from a biological sample, 2) in effector cells isolated from a biological sample and cultivated, or 3) in effector cells isolated from a biological sample, cultivated and modified. The modified effector cells can be genetically modified cells or malignantly transformed cells. The effector cells can be, for example, mast cells, basophils, eosinophils, T cells, B cells and Antigen Presenting Cells (APC), and combinations thereof;

a method of evaluating the immunological activity of a vaccine preparation wherein the vaccine is subjected solely to a measurement of the immunological activity of the mixture of the liquid phase and the solid phase, or the vaccine can be subjected solely to a measurement of the immunological activity of antigen in the liquid phase upon a treatment of the mixture to displace the antigen from the solid phase. Alternatively, the vaccine can be subjected both to a measurement of the immunological activity of the mixture of the liquid phase and the solid phase, and to a measurement of the immunological activity of antigen in the liquid phase. In another embodiment, the vaccine can be subjected both to a measurement of the immunological activity of antigen in the liquid phase and to a measurement of the immunological activity of antigen in the solid phase;

a method of evaluating the immunological activity of a vaccine preparation, wherein the displacing treatment comprises contacting the mixture with a protein-containing reagent or an anion. The protein-containing reagent can be, for example, a body fluid containing proteins. The body fluid can be, for example, blood serum. The anion can be, for example, phosphate ions;

a method according to any of the preceding methods, wherein the immunological activity of an antigen-containing intermediate product used for preparing the vaccine is measured, and wherein the evaluation of the immunological activity of the vaccine is based on a comparison of the measurement result obtained for the intermediate product and the measurement results obtained for one or more of measurements;

a method according to any of the preceding methods, wherein the vaccine is subjected to the measurements immediately upon preparation or, alternatively, immediately after preparation and after one or more periods of storage, and wherein the evaluation of the immunological activity of the vaccine is based on a comparison between the former and latter measurement results;

a method according to any of the preceding methods, wherein the evaluation of the immunological activity of the vaccine is based on a comparison between the measurement results obtained for the vaccine and prior corresponding measurement results from the same type of vaccine or from another type of vaccine;

a method according to any of the preceding methods, wherein the solid phase carrier is an oxygen-containing metal salt, such as, for example, aluminum hydroxide, calcium phosphate, or aluminum phosphate;

a method according to any of the preceding methods, wherein the molecular antigen is an allergen; and iii) optionally repeating steps i) and ii) until a desired immunological activity is obtained.

Also, the invention relates to a vaccine preparation obtainable by the method of preparing a vaccine preparation according to the invention.

DEFINITIONS

The expression "in vitro method" means a method, which may be carried out without immunizations of test animals.

The expression "immunological activity" means any response of the immune system, including allergenic activity and potential for inducing allergic reactions, including potential for inducing anaphylaxis.

The expression "allergenic activity" means IgE binding activity.

The expression "solid phase carrier" means any water-insoluble substance capable of forming a covalent and/or a non-covalent attachment with an antigen, wherein the non-covalent attachment includes e.g. adherence, inclusion, encapsulation and coupling.

The expressions "solid phase" and "liquid phase" of a vaccine mean the phases resulting from a separation process for the separation of a suspension of the solid phase carrier in the liquid into a solid phase and a liquid phase, the separation process being e.g. centrifugation, extraction or simple sedimentation.

The expression "attached" means any covalent and/or a non-covalent attachment, wherein the non-covalent attachment includes e.g. adherence, inclusion, encapsulation and coupling.

Methods and Materials

Preparation of Aluminum Gel Adjuvant Allergen Vaccines

Lyophilized allergen is dissolved in an aqueous buffer and diluted to a desired concentration. "Alhydrogel" (1.3%) is added to the allergen solution obtained while stirring, and then sterile water is added. The resulting solution is allowed to stand to the following day, and then buffer is added slowly while stirring to produce the final allergen aluminium aluminum hydroxide gel.

EXAMPLES

Example 1

IgE Inhibition Assay for Allergen in Solution and for Allergen Adsorbed to an Aluminum Hydroxide Gel Adjuvant Method IgE inhibition experiments were performed on an ADVIA centaur instrument. Serial dilutions (performed with the TECAN (P-05-07F294)) of the inhibitor (Antigen in solution or antigen gel adjuvant vaccine) were mixed with a fixed amount of biotinylated antigen and further incubated with a solid phase absorbed IgE. The amount of biotinylated allergen bound to the solid phase was estimated as the light emitted after incubation with streptavidin labelled with acridinium ester. The raw data was processed in Excel and transferred to GraphPad Prism v. 4.0 for the final analysis (curve fitting, plotting and statistical comparisons). The data was fitted to a four parameter logistic function (Eqn. 1), $$Y = B + \frac{T - B}{1 + 10^{(\log_{10} EC50 - \log_{10} X) * HillSlope}} \quad (1)$$

and fitted curves was considered parallel if the HillSlope (HS) of the individual fits did not differ significantly. EC50 was estimated from fits constrained with a common HS estimate. EC50 denotes the concentration resulting in 50% inhibition.

Results

The IgE inhibition assay described above was used for testing the immunological activity of Phl p allergen and Bet v allergen gel adjuvant vaccines. The results are shown in FIG. 1.

FIG. 1 shows the ability of Phl p extract adsorbed to an aluminum hydroxide gel (Alutard Phl p) to inhibit the binding of IgE to biotinylated Phl p extract using Phl p extract in solution (Phl p) as reference and Bet v extract (Alutard Bv) as negative control.

The allergen extract in solution was the extract used for preparing the gel adjuvant vaccine and was used for comparison purposes.

From FIG. 1 the following may be concluded: As the maximum inhibiting potential of the Phl p extract gel corresponds to that of Phl p extract in solution, it can be concluded that the present IgE inhibition immunoassay is capable of measuring the full level and the full scope of specificity of immunological activity of the Phl p extract gel. The negative control Bet v extract gel shows no inhibitory activity.

As will appear from FIG. 1, the inhibition curve of the allergen gel vaccine is shifted somewhat to the right, the course of the shifted curves being parallel to that of the allergen in solution. This means that a higher concentration of the gel formulated allergen is needed to obtain the same degree of inhibition.

Example 2

Histamine Release Assay for Allergen Adsorbed to an Aluminum Hydroxide Gel Adjuvant Method Histamine was measured in an ELISA-based method based on the competition between histamine to be assayed and its enzyme conjugate, histamine-alkaline phosphatase used as tracer for binding to antibody coated onto microwells. The monoamine histamine is too small to occupy completely the binding site on the antibody. High affinity monoclonal antibodies directed against modified histamine have therefore been obtained. The histamine in the sample must be derivatized in the same manner as the histamine of the conjugate. This is achieved readily and reproducibly with an acylating reagent at slightly alkaline pH. The acylated histamine of the sample, and the histamine-alkaline phosphatase conjugate, when added to the microtiter wells, compete for binding to a limiting number of antibody sites. After incubation, the wells are rinsed in order to remove non-bound components. The bound enzymatic activity is then measured by the addition of a chromogenic substrate (pNPP). The intensity of the color depends inversely on the concentration of histamine in the sample. The concentration is calculated on the basis of a standard curve obtained with standards. The enzyme immunoassay was carried out using a kit obtainable from "IMMUNOTECH" (Marseille, France).

Purpose:

Histamine release with aluminum hydroxide formulated allergen in conditions resembling in vivo conditions in the event that vaccine is accidentally given in the blood stream. This is accomplished by measuring histamine release in undiluted whole blood to which vaccine is added. After stimulation the cells are spun down, and supernatant containing histamine is separated off. Then the histamine concentration is measured using Immunotech ELISA kit 2015.

Reagents and Materials:

Pipes buffer pH 7.4 BB LAB97350

14 ml Falcon PP tubes

Venojekt heparin stabilized blood glass VT-100SH

PP Polypropylene Round bottom culture test tube: Elkay 12×75 mm 0002053001

PP stoppers

Immunotech ELISA kit 2015

ELISA washer ELP-40

ELISA reader EL-340 with KC4 program

Centrifuge with rotor for plates: Sigma 3-15

Incubator 37° C.

Coca 0.5%

Shaking table Titramax 1000

Various single-, 8- and 12-channel pipettes

Release:

Heparin stabilized whole blood was pre-heated to 37° C. Aliquots of various vaccines and controls were diluted 1:200 in Coca buffer. 2 µl were pipetted into Falcon tubes and diluted 1:500 in freshly drawn, undiluted whole blood. Incubation was performed at 37° C. for 30 min.

Centrifugation:

The tubes were centrifuged for 10 min. at 800×g. The supernatants were collected and assayed using the histamine ELISA histamine.

ELISA Determination:
1. Acetylation of samples and standards:
Standards are pipetted into the plates with samples
+25 µl acetylation buffer is added by pipettes
+25 µl acetylation reagent
2. Thorough mixing with 12 channel pipette and 50 µl is transferred to pre-coated ELISA plate.
3. 200 µl Histamine conjugate pr. well is added
4. Incubation at 2-8° C. in refrigerator
   either a: on shaking table >2 times
   or b: without shaking >18 times
5. Washing on ELISA micro titer cell plate washer program: "Bot-wa-no-res 12" with the above washing buffer.
6. 200 µl color substrate pr. well is added
7. Incubation at 18-25° C. (covered) on shaking table in 30 min.
8. Reaction stopped by adding 50 µl Stop solution.
9. Reading on Reader with KC4 software (Bio-Tek, Inc.) at 405 nm.
10. Concentration is calculated in KC4 software (Bio-Tek, Inc.) by linear fitting of standard curve.

Results

In a first experiment, a vaccine in the form of Phl p extract allergen adsorbed to aluminum hydroxide gel adjuvant (Vaccine A), the supernatant of Vaccine A after sedimentation, and the solid phase of Vaccine A after sedimentation were assayed using the histamine release assay described above. The supernatant and solid phase samples were obtained as follows: Vaccine A was allowed to stand for a period of three days in a vial to precipitate the gel phase, and a sample was taken with a syringe from the top of the vial, and from the bottom of the vial, respectively. The results are shown in FIG. 2.

Figure 2:
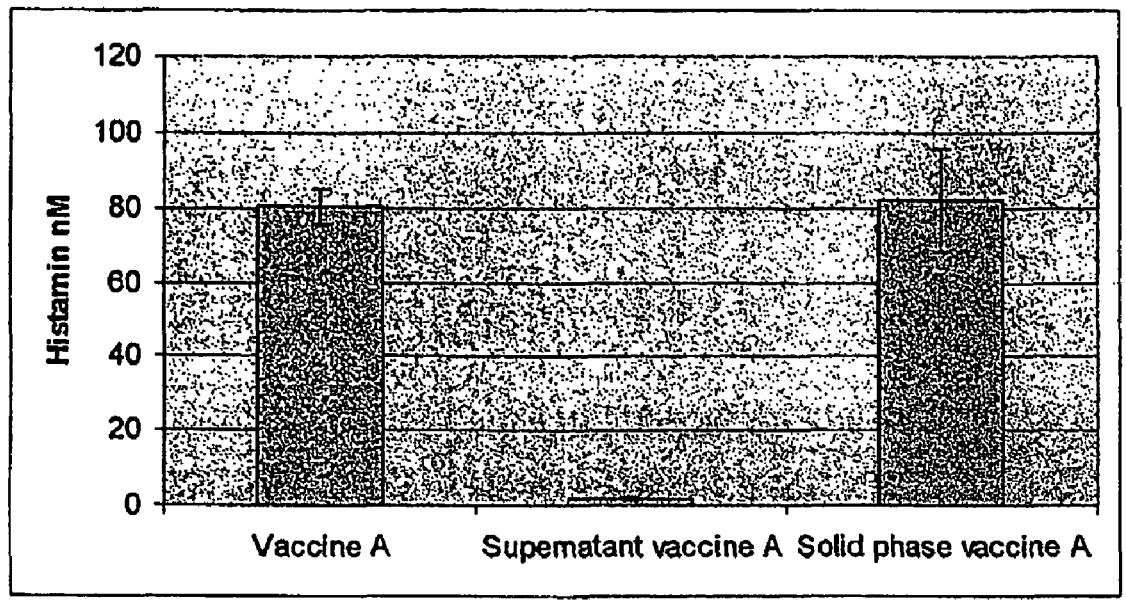
FIG. 2 shows histamine release levels of a vaccine in the form of Phl p extract allergen adsorbed to aluminum hydroxide gel adjuvant (Vaccine A), of the supernatant of Vaccine A after sedimentation, and of the solid phase of Vaccine A after sedimentation.

As will appear from FIG. 2, only a very small amount of the allergen is present in the supernatant, and almost all of the allergen is present in the gel phase of the vaccine. This is indicative of an effective and safe depot vaccine.

In a second experiment, a vaccine in the form of Phl p extract allergen adsorbed to aluminum hydroxide gel adjuvant (+alum) and Phl p extract allergen in solution (−alum) were assayed using the histamine release assay described above. The results are shown in FIG. 3.

Figure 3:
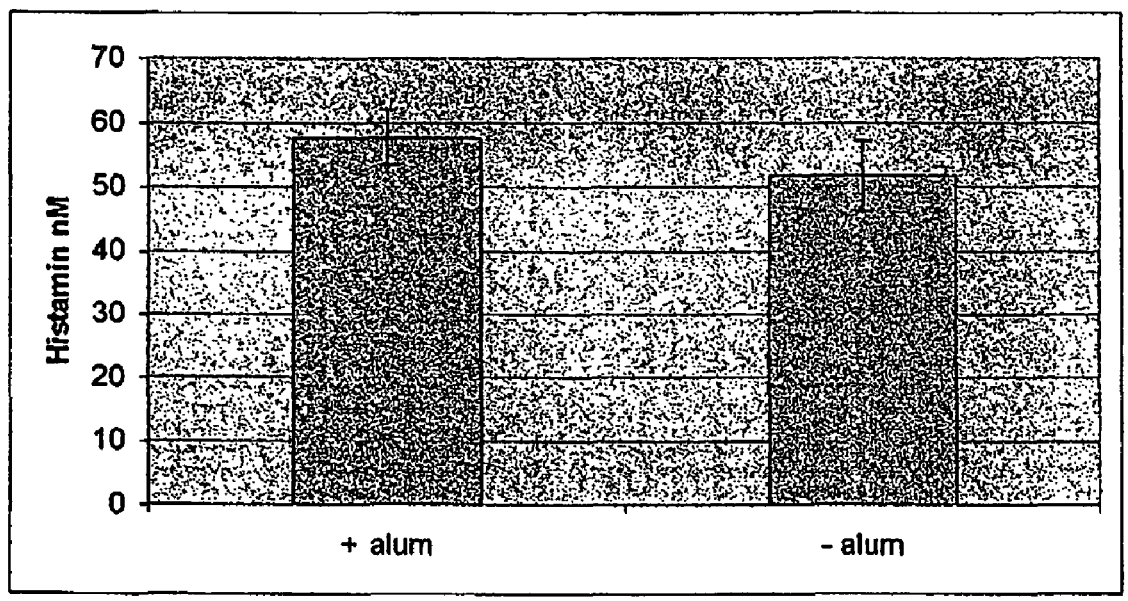
FIG. 3 shows the histamine release levels of a vaccine in the form of Phl p extract allergen adsorbed to aluminum hydroxide gel adjuvant (+alum) and of Phl p extract allergen in solution (−alum).

As will appear from FIG. 3, the histamine release elicited by the allergen gel vaccine is of the same level as that of the allergen solution, and hence the present histamine assay is capable of measuring the full allergenic activity of the gel vaccine.

Example 3

T Cell Proliferation Assay for Allergen Adsorbed to an Aluminum Hydroxide Gel Adjuvant T-Cell Assay:

Early events in the T-cell activation were investigated through flow cytometric analysis of T-cell expression of the surface receptor CD69, which are up-regulated at different time-points during T-cell activation.

Flow cytometric analysis is based on the attachment of fluorescence conjugated anti-surface marker antibodies to the cell surface and subsequent detection of the level fluorescence intensity on the individual cell by FACS analysis.

Phl p extract vaccines and supernatants of Phl p extract vaccines stored for 14 months, 8 months, 4 months and 1 month were tested. Also, two Phl p extracts (IMP 1 and IMP 4), purified Phl p 1 and purified Phl p 5 in solution were tested. Superantigen (SEB) and medium (med) were as references.

Figure 4:
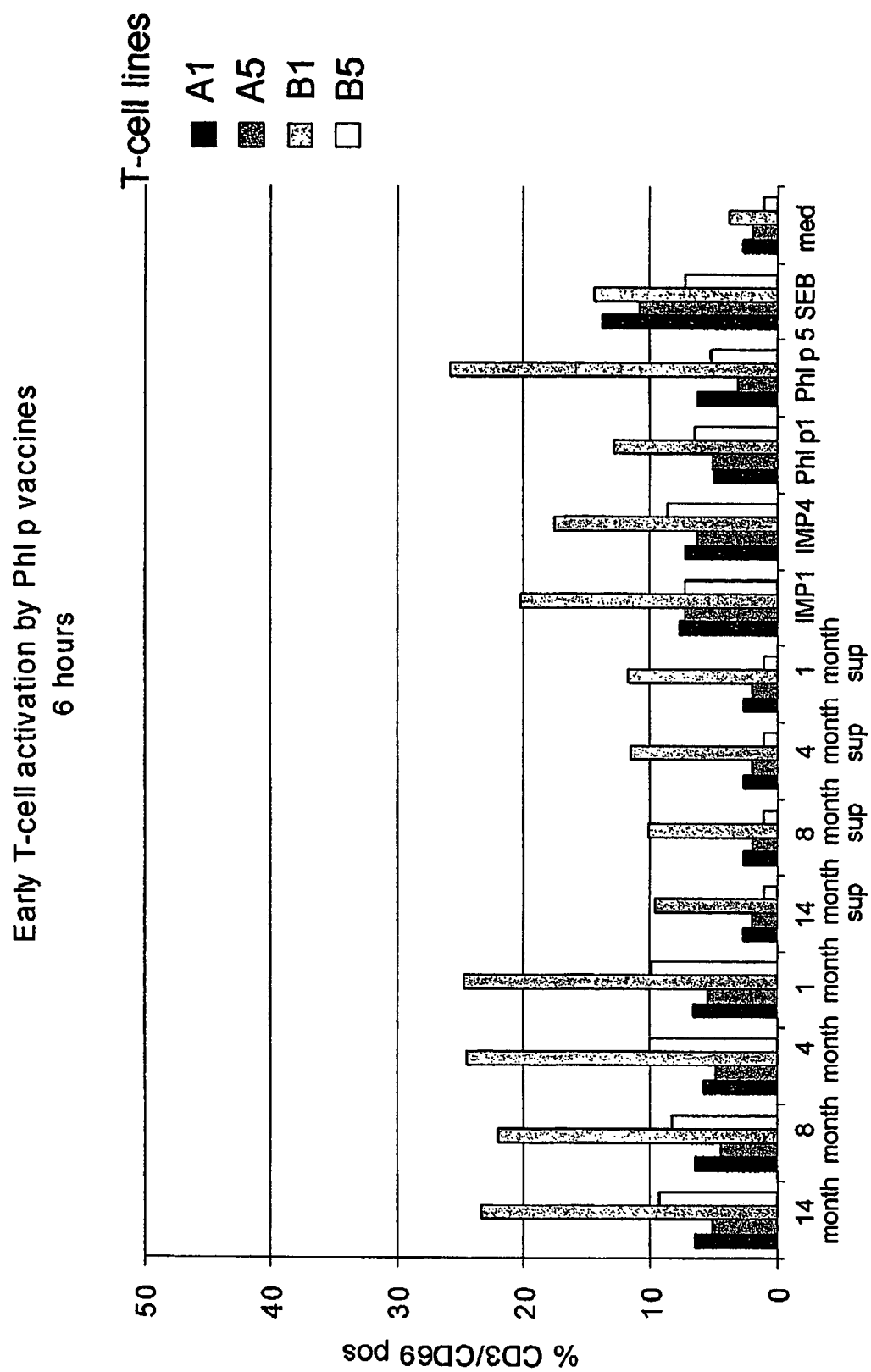
FIG. 4 shows T cell stimulation using CD69 as marker for four Phl p extract aluminum gels, the supernatants thereof, for two Phl p extracts in solution and for purified Phl p 1 and Phl p 5 in solution.

Results:

Four different T-cell lines where stimulated with complete grass vaccines or the supernatants of the vaccines obtained after centrifugation. The age of the vaccines differed from 1 to 14 month after end of production and the percentage of T-cells (CD3+) expressing CD69 was used as readout. The results are shown in FIG. 4, which clearly demonstrates that vaccines of different age induce comparable T-cell activation and that it is possible to distinguish between the potential of the complete vaccine and the related supernatants. In addition, the complete vaccines induce T-cell activation at the same level as the crude extracts (IMP1 and 4). The purified allergens Phl p 1, Phl p 5, and the super-antigen SEB are included as controls. In subsequent experiments it was shown that aluminum hydroxide gel without allergen does not induce CD69 expression on allergen-specific T-cells.

Example 4

Displacement (Desorption) of Allergen Adsorbed to an Aluminum Hydroxide Gel Adjuvant Materials:

Two aluminum hydroxide gel vaccines (Alutard) comprising the allergens Phl p 1 and Phl p 5 were tested. The displacement agents used were: 200 mM phosphate (NAH2PO4-Na2HPO4) buffer pH 7.4 diluted (in the sample vaccine) to either 5.0 mM or 50 mM phosphate buffer, serum pool constructed from samples from non allergic individuals (AG-525-) or serum pool containing 5 mM phosphate.

Methods:

The displacements were performed as follows: A vaccine (1 mL) was mixed either with an appropriate volume of 200 mM phosphate buffer yielding a final phosphate concentration of 5 or 50 mM and incubated 1 or 20 hours at 37° C.; or diluted 1:1 with either serum pool alone or serum pool and an appropriate volume of 200 mM phosphate buffer yielding a final phosphate concentration of 5 mM. After incubation the samples were centrifuged (10 min, 4000 rpm) and the supernatant was harvested and stored at −20° C. until used. Samples serving as reference or zero points were just centrifuged and the supernatant was stored at −20° C. until used.

The amount of the individual allergens Phl p 1 and Phl p 5 were determined from inhibition experiments, in short: Standard curves for each allergen were obtained from inhibition experiments using biotinylated purified allergen inhibited with purified allergen. The data was fitted to a four parameter logistic function (Eqn. 1) and the inhibitory capacity measured for a given displacement supernatant was transformed into an allergen concentration using equation 1 and the parameters determined for each allergen. All the estimated concentrations were then corrected for dilutions with the displacement agents and all reported figures refer to the amount in 1 mL vaccine.

$$Y = B + \frac{T - B}{1 + 10^{(\log_{10} EC50 - \log_{10} X) * HillSlope}} \quad (1)$$

Figure 5:
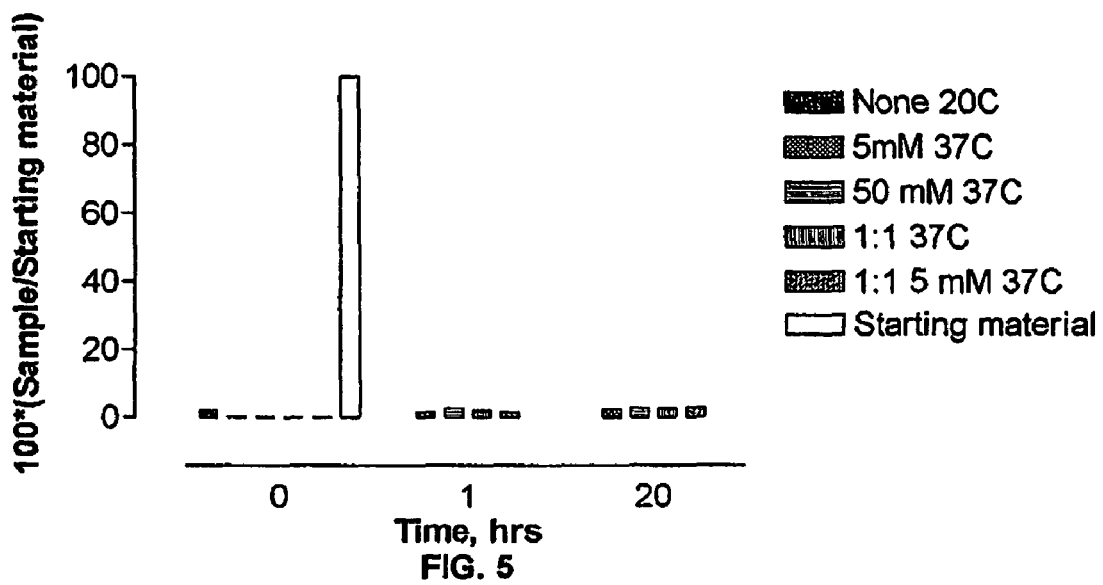
FIG. 5-6 show the displacement (desorption) of allergen from aluminum hydroxide gel vaccines (Alutard) comprising the allergens Phl p 1 and Phl p 5, respectively.
Figure 6:
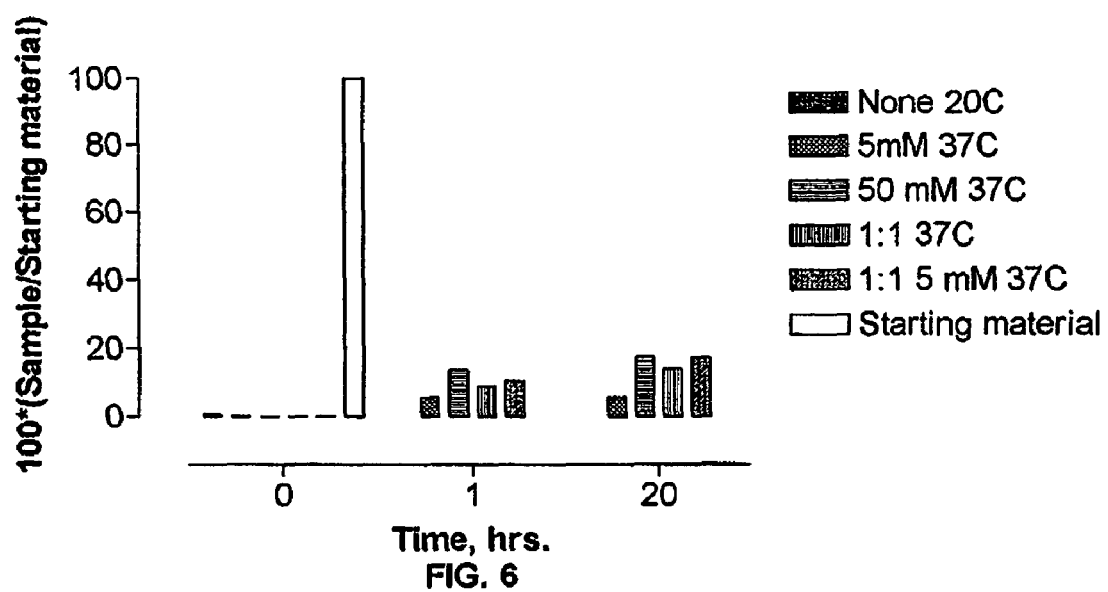

Results:

The results are shown in FIGS. 5 and 6 using the following denominations: None: signifies no treatment of the sample, 1:1: signifies displacement performed with human serum and the molar figures refer to the final concentration of phosphate buffer. Also, the temperature is indicated. All figures represent the amount in the initial samples (dilution corrected).

As will appear from FIGS. 5 and 6, the displacement of Phl p 1 from the aluminum hydroxide gel is much lower than the displacement of Phl p 5. However, in both cases the level of displacement is low. This is indicative of an effective and safe depot vaccine.

The invention claimed is:

1. A method for evaluating a vaccine preparation for the ability to induce an antibody response in a subject administered the vaccine comprising:
   i) providing a vaccine preparation to be evaluated, which vaccine preparation comprises a mixture of a molecular antigen and a carrier, wherein the mixture comprises a liquid phase and a solid phase to which at least a portion of the molecular antigen is attached; and
   ii) performing at least one of the steps selected from the group consisting of:
      1) measuring the in vitro antibody binding capacity of the mixture,
      2) measuring the in vitro antibody binding capacity of the solid phase,
   wherein measuring the in vitro antibody binding capacity comprises performing an immunoassay employing an antibody bound to a particulate antibody solid phase, the antibody being specific to the molecular antigen of the vaccine preparation.

2. The method according to claim 1, wherein the provided vaccine preparation has been treated to displace the molecular antigen from the solid phase.

3. The method according to claim 2, wherein the treatment to displace the molecular antigen from the solid phase comprises contacting the mixture with a protein-containing reagent.

4. The method according to claim 3, wherein the protein-containing reagent is a body fluid that contains proteins.

5. The method according to claim 4, wherein the body fluid is blood serum.

6. The method according to claim 2, wherein the treatment to displace the molecular antigen from the solid phase comprises contacting the mixture with an anion.

7. The method according to claim 6, wherein the anion is a phosphate ion.

8. The method according to claim 1, wherein the molecular antigen is an allergen.

9. The method according to claim 8, wherein the allergen is selected from the group consisting of tree pollen allergens, grass pollen allergens, herb pollen allergens, mite allergens, venom allergens, animal hair allergens, animal dandruff allergens, and food allergens.

10. The method according to claim 9, wherein the allergen is a grass pollen allergen.

11. The method according to claim 9, wherein the allergen is a dust mite allergen.

12. The method according to claim 9, wherein the allergen is a mixture of at least two different allergens.

13. The method according to claim 8, wherein the allergen is in the form of an extract, a purified allergen, a modified allergen, a recombinant allergen, a mutant of a recombinant allergen, or any combination thereof.

14. The method according to claim 13, wherein the allergen is in the form of an extract.

15. The method according to claim 1, wherein the carrier is an oxygen-containing metal salt.

16. The method according to claim 15, wherein the oxygen-containing metal salt is aluminum hydroxide, calcium phosphate, or aluminum phosphate.

17. The method according to claim 1, wherein the molecular antigen-specific antibody bound to the particulate antibody solid phase is selected from the group consisting of IgA, IgE, IgG, IgM and combinations thereof.

18. The method according to claim 17, wherein the molecular antigen-specific antibody bound to the particulate antibody solid phase is IgG.

19. The method according to claim 17, wherein the molecular antigen-specific antibody bound to the particulate antibody solid phase is IgE.

20. The method according to claim 17, wherein the molecular antigen-specific antibody bound to the particulate antibody solid phase is a combination of IgE and IgG.

21. The method according to claim 1, wherein the immunoassay is a competitive immunoassay.

22. A method for evaluating a vaccine preparation for the ability to induce an antibody response in a subject administered the vaccine comprising:

i) providing a first vaccine preparation to be evaluated, which vaccine preparation comprises a mixture of a first molecular antigen and a first carrier, wherein the mixture comprises a liquid phase and a solid phase to which at least a portion of the first molecular antigen is attached;
ii) providing a second vaccine preparation to be evaluated, which second vaccine preparation comprises a mixture of a second molecular antigen and a second carrier, wherein the mixture comprises a liquid phase and a solid phase to which at least a portion of the second molecular antigen is attached;
iii) performing at least one of the steps selected from the group consisting of:
  1) measuring the in vitro antibody binding capacity of the first vaccine preparation mixture and of the second vaccine preparation mixture, and
  2) measuring the in vitro antibody binding capacity of the first vaccine preparation solid phase and of the second vaccine preparation solid phase,
wherein measuring the in vitro antibody binding capacity comprises performing an immunoassay employing an antibody bound to a particulate antibody solid phase, the antibody being specific to either the first molecular antigen of the first vaccine preparation, or to the second molecular antigen of the second vaccine preparation; and
iv) comparing the measured in vitro antibody binding capacity of the first and second vaccine preparations.

23. The method of claim 22, wherein at least one of the provided vaccine preparations has been treated to displace the molecular antigen from the solid phase.

24. The method of claim 22, wherein at least one of the molecular antigens is an allergen.

25. The method of claim 22, wherein the first molecular antigen and the second molecular antigen are the same molecular antigen.

26. The method of claim 22, wherein at least one of the carriers is an oxygen-containing metal salt.

* * * * *